US00PP31065P3

(12) United States Plant Patent
Hansen

(10) Patent No.: US PP31,065 P3
(45) Date of Patent: Nov. 12, 2019

(54) **X *HEUCHERELLA* PLANT NAMED 'CATCHING FIRE'**

(50) Latin Name: **X *Heucherella* (*Heuchera* x *Tiarella*)**
Varietal Denomination: Catching Fire

(71) Applicant: Hans A. Hansen, Zeeland, MI (US)

(72) Inventor: Hans A. Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 78 days.

(21) Appl. No.: 15/530,533

(22) Filed: Jan. 25, 2017

(65) Prior Publication Data

US 2018/0213706 P1 Jul. 26, 2018

(51) Int. Cl.
*A01H 5/02* (2018.01)
*A01H 6/80* (2018.01)

(52) U.S. Cl.
USPC ..... Plt./441
CPC ..... *A01H 6/80* (2018.05)

(58) Field of Classification Search
USPC ..... Plt./441
CPC ..... A01H 6/80
See application file for complete search history.

*Primary Examiner* — Keith O. Robinson

(57) ABSTRACT

The new hybrid X *Heucherella* plant named 'Catching Fire' with rugose, downwardly-cupped, palmately-lobed foliage changing from vibrant yellow with cherry-red flame surrounding the veins in the spring to lime-green with mahogany pattern around veins. 'Catching Fire' is vigorous and produces many airy panicles with numerous sterile creamy-white flowers beginning late spring and exhibits good heat and humidity tolerance. The plant is useful for landscaping as a specimen color, en masse, or as a container plant.

1 Drawing Sheet

Botanical denomination: X *Heucherella* (*Heuchera* x *Tiarella*).

Cultivar designation: 'Catching Fire'.

BACKGROUND OF THE INVENTION

The present invention relates to a new and distinct intergeneric hybrid between coral bells and foam flower, both in the Saxifragaceae family and given the cultivar name of 'Catching Fire' with the combined generic epithet X *Heucherella*. X *Heucherella* 'Catching Fire' resulted from an intentional cross between a proprietary unreleased hybrid known as *Heuchera* K10-74-23 (not patented) as the female or seed parent and a proprietary unreleased seedling *Tiarella* 'Jade Peacock' U.S. Plant Pat. No. 26,730 as the male or pollen parent. The new plant was hybridized by the inventor at a wholesale perennial nursery in Zeeland, Mich., USA on Feb. 11, 2013. The new plant was selected from among many other crosses and X *Heucherella* seedlings growing at the same nursery which met the rigorous criteria of excellent foliage, vigor and habit established as breeding goals and was originally assigned the breeder code of 13-212-2.

X *Heucherella* 'Catching Fire' has been asexually propagated by basal cutting at a nursery in Zeeland, Mich. and also by sterile tissue culture propagation. The resultant asexually propagated plants have remained stable and exhibit the same characteristics as the original plant over multiple generations.

BRIEF SUMMARY OF THE INVENTION

X *Heucherella* 'Catching Fire' differs from its parents as well as all other X *Heucherella* known to the applicant. The most similar cultivars are X *Heucherella* 'Stoplight' U.S.

Plant Pat. No. 16,835, 'Sunspot' U.S. Plant Pat. No. 14,825, 'Leapfrog' (not patented) and 'Alabama Sunrise' U.S. Plant Pat. No. 19,611. Compared to the female parent, *Heuchera* K10-74-23 and all the grandparents, the new plant has more rugose leaves with more yellow leaf margins with brick red color in the center running along the major veins and the flowers are whiter and have thinner petals and calyx segments. Compared to the male parent, the new plant has less dissected and more yellowish foliage with taller scapes compared to the green foliage and shorter scapes than those of *Tiarella* 'Jade Peacock'. 'Stoplight' has leaves that are less rugose and as juvenile with less acute apices. 'Sunspot' has leaves that are much flatter and less rugose, the lobes are longer and deeper incised and the flower is pink rather than cream. Compared with 'Leapfrog' the new plant has more narrow and brighter red surrounding the veins, and the leaves are more rugose on the new plant. 'Alabama Sunrise' has leaves with more chartreuse and not as bright yellow, the lobes are more deeply dissected and longer than the new plant. The leaf blades of the new plant tend to be more cupped downward than all of the above comparison plants.

The new plant differs from all *Heuchera*, X *Heucherella* and *Tiarella* known to the inventor in the following combined traits:

1. The foliage is a vibrant yellow with cherry-red flame-shaped markings surrounding the veins.
2. Leaves mature to a lime-green with mahogany pattern around the veins.
3. The leaf blades are rugose and cupped slightly downward.
4. The flowers are creamy-white on branched panicles.
5. Habit is mounded with multiple tightly clustered shoots emerging at the base all season.

6. The plant is robust, seedless, compact and is more heat tolerant than typical X *Heucherella*.

BRIEF DESCRIPTION OF THE DRAWING

The photographs of the new plant demonstrate the overall appearance of the plant including the unique traits. The plant in the photograph is of a one-year-old plant grown at a wholesale perennial nursery in Zeeland, Mich., USA. The colors are as accurate as reasonably possible with color reproductions. Some slight variation of color may occur as a result of lighting quality, intensity, wavelength, and direction or reflection.

DETAILED BOTANICAL DESCRIPTION

Figure 1:
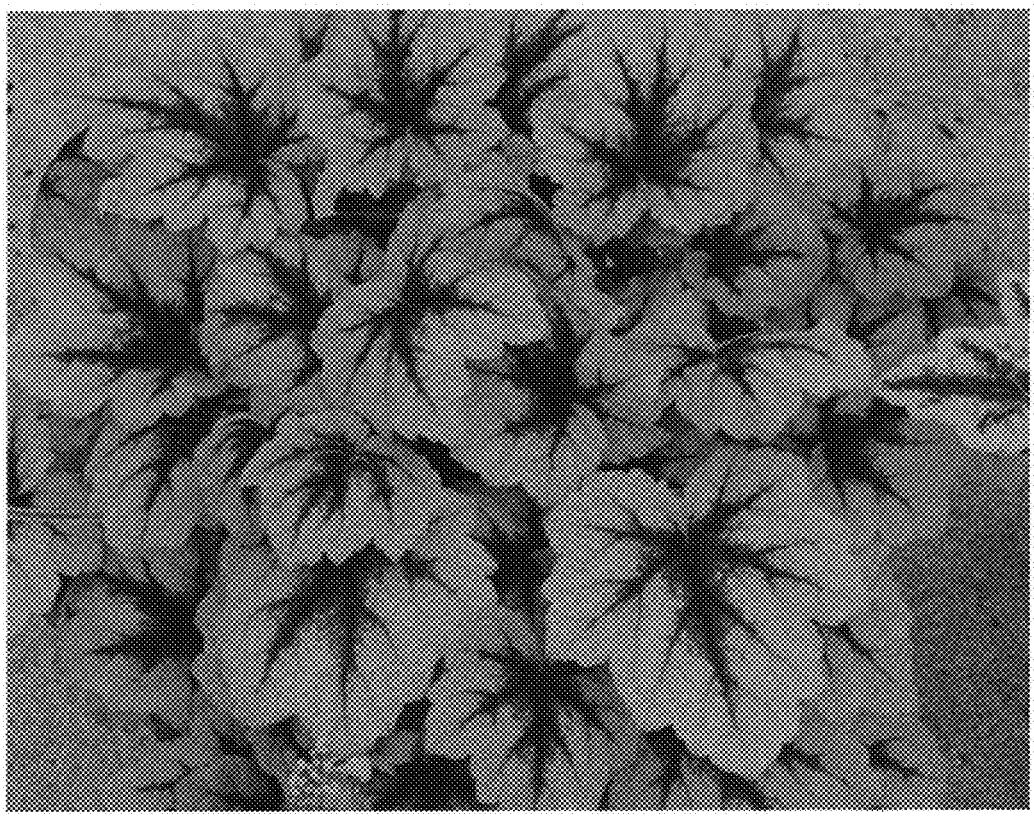
FIG. 1 shows a one-year-old plant greenhouse grown as beginning to flowering.
Figure 2:
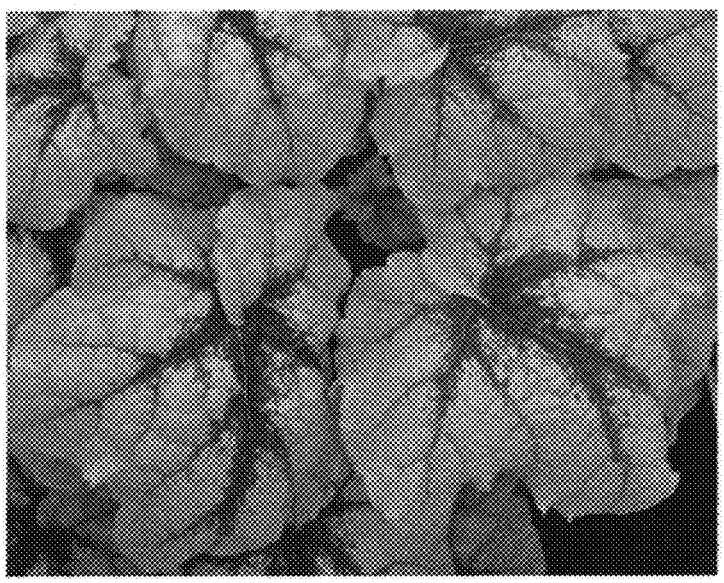
FIG. 2 shows a close-up of the foliage early spring prior to flowering.

The following description is based on one-year-old plants growing in double poly greenhouse with supplemental water and fertilizer at a wholesale perennial nursery in Zeeland, Mich., USA as well as outdoor trial garden grown plants for seasonal foliage coloration comparisons. 'Catching Fire' has not been grown under all possible environments and may phenotypically appear different under different conditions such as light, temperatures, fertilizer, and water, without any difference in genotype. The color descriptions are from the 2001 edition of The Royal Horticultural Society Colour Chart except where common dictionary terms are used.

Parentage: The female or seed parent, *Heuchera* K10-74-23, consists of genes from 'Southern Comfort' U.S. Plant Pat. No. 20,364, 'Pinot Gris' U.S. Plant Pat. No. 19,592 and 'Encore' U.S. Plant Pat. No. 19,578; the male or pollen parent was *Tiarella* 'Jade Peacock';

Plant habit: Hardy herbaceous perennial of tightly compact rhizomes with basal rosette of mounded foliage; foliage about 18.0 cm tall and 34.0 cm across;

Roots: Fibrous, finely branched; when actively growing near white in color depending on soil type, nearest RHS 158D;

Growth rate: Rapid, rooting from cutting in 2 weeks and finishing in three-liter container in about 3 months;

Foliage: Palmately lobed; pubescent abaxial and adaxial; lobes shallowly dissected to less than one quarter of the way to petiole; matte surface above and below, glossiness; lobe apices rounded in maturity and acute as juvenile; cordate base with lobes imbricate about 1.0 cm; blade to about 10.0 cm long and 10.5 cm wide, average about 8.5 cm long and 9.0 cm wide; with a dark red pigment nearest RHS 187C surrounding the veins and expanding in width and density from stippling to solid pattern as foliage matures though season; center lobe about 4.0 cm long and about 4.0 cm wide; cauline leaves at up to first five nodes below flowers and decreasing in size distally; foliage density medium;

Foliage margin indentations: Shallowly lobed;

Foliage color: Leaf color is seasonally variable; spring young emerging leaves adaxial nearest RHS N170B with a center inner palm pigmenting surrounding the base of main veins nearest RHS 187C; abaxial spring emerging leaves between RHS 174C and RHS 174B; when first flowering adaxial center surround the veins nearest RHS 187B and remainder of blade between veins between RHS 151A and RHS 151B; when first flowering abaxial leaves area surrounding veins nearest RHS 187B with undertone of nearest RHS 145C and area between veins nearest RHS 145A; late fall and winter adaxial area surrounding veins nearest RHS N187A and area between veins closest to petiole nearest RHS 137B; late fall and winter and abaxial area surrounding veins closest to petiole nearest RHS N187B with undertone of RHS 138B and surrounding area between RHS 138A and RHS 138B;

Leaf margin: Serrate as juvenile and crenate when mature, ciliate;

Leaf apex: Acute as juvenile and rounded when mature; minutely cuspidate to with spicule;

Leaf base: Cordate with lobes sometimes imbricate by about 5.0 mm;

Leaf surface: Pubescent abaxial and adaxial; rugose;

Leaf quantity: About six per division and 60 per plant;

Veins: Palmate, puberulent adaxial and pubescent abaxial;

Vein color: Adaxial early season nearest RHS 174D, abaxial early season nearest RHS N170D; flowering season adaxial nearest RHS 145C, flowering season abaxial nearest RHS 145C; winter season adaxial nearest RHS 191B, and winter season abaxial nearest RHS 147C;

Petiole: Cylindrical, hirsutulous, about 13.0 cm long and 2.5 mm diameter; wiry but flexible;

Petiole color: On emerging foliage nearest RHS 187B; mid-flowering season nearest RHS 176A and late fall and winter blend between RHS 183B and RHS N187B;

Inflorescence: In open branched panicle, about ten panicle per plant; about 150 flowers per panicle; first panicle flowering beginning late May in Michigan and remaining in flower for about three weeks; individual flowers remaining open about three to four days; plant remains in flower with new panicles for about five weeks;

Fragrance: None detected;

Peduncle: Round in cross section; hirtellous; about 45 cm tall and 15 mm diameter at base, flowering portion about 28 cm tall and 3.5 cm wide; with cauline leaves at lower three to five nodes; mostly upright; flower density medium;

Peduncle color: Nearest RHS 145A below foliage and developing between RHS 182A and RHS 182C in distal region;

Peduncle branches: At lower half of peduncle; with branches at lowest one to three nodes flowering about one week after the main peduncle begins; lowest branch with about 12 flowers, about 3.0 cm long and 1.5 mm diameter; decreasing in flower quantity and overall length distally;

Cauline leaves: To about 6.5 cm across and 8.5 cm long with petioles about 10.0 cm long and 1.5 mm diameter at base, decreasing distally; color of cauline leaves and petioles same as other foliage with burgundy surrounding veins not extending into leaves as far and not as wide;

Pedicel: Round in cross section; glandular, hirtellous; about 2.0 mm long and 0.8 mm diameter;

Pedicel color: Variable between RHS 182C and RHS 186D;

Buds one day prior to opening: Oblong, about 3.5 mm long and 2.0 mm diameter;

Bud color: Distal two third closest to RHS 155A greening at base to between RHS 145B and RHS 145C;

Flower: Perfect, campanulate; about 5.5 mm deep and 7.0 mm in diameter at face; individual flowers lasting about three to four days on plant or as cut flower; attitude outwards;

Calyx: Five sepals; glandular outside, glabrous inside; apex acute, fused at base into hypanthium; margin entire;

sepals about 3.5 mm long and 1.0 mm wide, calyx about 5.0 mm across and 3.0 mm deep;

Calyx color: Inside and outside lighter than RHS 155D;

Petals: Typically four or five; spatulate, narrowly acute apex, attenuate base; margin entire; minutely pubescent outside and glabrous inside; about 5.5 mm long and 0.8 mm wide;

Petal color: Abaxial lighter than RHS N155D; adaxial near white, lighter than RHS N155D;

Androecium:

*Filaments*.—Typically five, thin, about 5.0 mm long and less than 0.5 mm in diameter; color white, lighter than RHS N155D.

*Anthers*.—Vestigial; oblong to nearly 0.5 mm long and less than half as wide; color nearest RHS 158A.

*Pollen*.—Not observed.

Gynoecium:

*Pistil*.—One central two-beaked pistil, about 5.0 mm long and 0.2 mm at apex flaring to 1.5 mm at base; color nearest RHS 155D.

*Stigma*.—Minute, about 0.2 mm diameter; color nearest RHS 155D.

*Ovary*.—Two carpels; apex tapering to meet pistil; rounded base and sides; about 1.5 mm across at widest point at base and 2.0 mm tall; color nearest RHS 155D.

Fruit and seed: Not observed;

Growth conditions: X *Heucherella* 'Catching Fire' grows best with ample moisture and drainage in either filtered or part sun. Cold hardy from USDA zones 4 to 9. X *Heucherella* 'Catching Fire' is able to tolerate heat and humidity better than many *Heucherella*.

Disease and pest tolerance: Other pest and disease resistance and tolerance outside of that normal for X *Heucherella* is not known. The new plant may be susceptible to diseases and pests common to other X *Heucherella*.

It is claimed:

1. The new and distinct ornamental plant named X *Heucherella* 'Catching Fire' as herein described and illustrated.

* * * * *